(12) United States Patent
Chinn et al.

(10) Patent No.: US 7,081,133 B2
(45) Date of Patent: Jul. 25, 2006

(54) ANTIBIOTIC TREATED IMPLANTABLE MEDICAL DEVICES

(75) Inventors: Joseph Andrew Chinn, Austin, TX (US); R. Michael Casanova, Austin, TX (US)

(73) Assignee: Carbomedics Inc., Austin, TX (US)

( * ) Notice: Subject to any disclaimer, the term of this patent is extended or adjusted under 35 U.S.C. 154(b) by 1148 days.

(21) Appl. No.: 09/746,712

(22) Filed: Dec. 21, 2000

(65) Prior Publication Data

US 2001/0003007 A1    Jun. 7, 2001

Related U.S. Application Data

(63) Continuation-in-part of application No. 09/359,235, filed on Jul. 22, 1999, now Pat. No. 6,528,107, which is a continuation-in-part of application No. 09/232,922, filed on Jan. 19, 1999, now abandoned, which is a continuation-in-part of application No. 09/605,804, filed on Jun. 28, 2000, now abandoned.

(51) Int. Cl.
    *A61F 2/24* (2006.01)
(52) U.S. Cl. ....................................... 623/2.41
(58) Field of Classification Search ................ 623/2.1, 623/2.41
    See application file for complete search history.

(56) References Cited

U.S. PATENT DOCUMENTS

| 5,301,664 | A |   | 4/1994 | Sievers et al. ......... 128/200.23 |
| 5,533,538 | A |   | 7/1996 | Marshall .................. 134/104.4 |
| 5,624,704 | A |   | 4/1997 | Darouiche et al. ......... 427/2.24 |
| 5,639,441 | A |   | 6/1997 | Sievers et al. ............... 424/9.3 |
| 5,948,019 | A | * | 9/1999 | Shu et al. .................. 623/2.41 |
| 6,585,767 | B1| * | 7/2003 | Holley et al. .............. 623/2.41 |

FOREIGN PATENT DOCUMENTS

WO    WO00/54745    9/2000

OTHER PUBLICATIONS

Irwin et al., "Long Term Evaluation of Prosthetic Mitral Valves in Sheep," *J. Invest. Surgery* 6:133-141 (1993).

* cited by examiner

*Primary Examiner*—Corrine McDermott
*Assistant Examiner*—Thomas Sweet
(74) *Attorney, Agent, or Firm*—Williams, Morgan & Amerson, P.C.

(57) ABSTRACT

Pannus-resisting implantable medical devices comprise one or more antimicrobial reservoirs, each such reservoir incorporating antimicrobial substances in predetermined distributions for timed release in vivo. Predetermined distributions of antimicrobial substances incorporated in antimicrobial reservoirs are achieved through use of fluid solvent carriers, which may comprise supercritical fluid solvents. Precipitation of antimicrobial substances from such solvent carriers in predetermined distributions is accomplished through evaporation and/or application of heating, cooling or decreased ambient pressure to the solvent carriers.

4 Claims, 5 Drawing Sheets
(3 of 5 Drawing Sheet(s) Filed in Color)

ANTIBIOTIC TREATED IMPLANTABLE MEDICAL DEVICES

This application is a continuation-in-part application of copending U.S. patent application Ser. No. 09/359,235, filed Jul. 22, 1999, now U.S. Pat. No. 6,528,107, which is a continuation-in-part application of U.S. patent application Ser. No. 09/232,922, filed Jan. 19, 1999, now abandoned. This application is also a continuation-in-part application of copending U.S. patent application Ser. No. 09/605,804, filed Jun. 28, 2000 now abandoned.

FIELD OF THE INVENTION

This invention generally concerns medical devices intended for implantation into patients. More particularly, this invention relates to incorporation of antimicrobial substances in medical devices to inhibit pannus overgrowth on or near the medical device after its implantation.

BACKGROUND

Implantable medical devices have become critical in the management of a variety of human diseases and other conditions. The term "implantable medical device" refers to a medical device that is intended for long-term implantation within the body of a patient, i.e., implantation for periods substantially exceeding one month. One significant class of implantable medical devices is prosthetic heart valves, which are used to replace diseased and/or damaged natural heart valves. Implantable medical devices also include annuloplasty rings, internal pacemakers, and artificial hip and knee prostheses, among others. The term "insertable medical device" refers to a medical device, that may be placed within the body of a patient for short-term periods, typically a few days but less than one month. Insertable medical devices include venous and urinary catheters, among others.

Although their development has saved countless thousands of lives and improved the quality of life for millions of patients, implantable medical devices do have certain risks of complications, including inflammatory tissue responses to the implant. Serious inflammatory tissue responses following implantation occur relatively infrequently in humans, but when present they can produce costly complications resulting in the need to remove and replace the implanted device or otherwise surgically intervene to correct the complication.

Prominent among post-operative complications is the excessive growth of tissue on implantable medical devices. In the case of prosthetic heart valves, there is a need for a moderate amount of tissue ingrowth into the sewing cuff of the valve to ensure that the valve remains anchored to the heart. The end-stage healing response to biomaterials such as the heart valve sewing cuff is fibrous encapsulation of the biomaterial. When integrated with the fabric, the connective tissue that constitutes the fibrous capsule is called pannus.

Incomplete pannus leaves fabric exposed, which can lead to chronic inflammation. Excessive pannus growth, on the other hand, occupies the orifice area distrupting blood flow, which can lead to thrombosis. In addition to an increased risk of thrombosis, overgrowth of pannus onto the prosthetic valve leaflets after implantation can lead to malfunction of the valve. More specifically, pannus overgrowth can protrude into the valve annulus and reduce the annular flow area, thus interfering with valve leaflet sealing. Limited control of pannus growth on implanted medical devices has been achieved through use of Biolite® carbon coating on device surfaces, but better control of pannus growth is desirable.

SUMMARY OF THE INVENTION

Experimental evidence has unexpectedly revealed that implantable prosthetic devices having sewing cuffs treated with certain antibiotics can prevent or reduce the severity of complications associated with pannus overgrowth. For example, sewing cuffs for prosthetic heart valves and annuloplasty rings may be fabricated of polyester, such as polyethylene terephthalate (PET), polytetrafluroethylene (PTFE), and/or silicone elastomers treated with antibiotics such as rifampin and/or minocycline.

An implantable prosthetic heart valve having resistance to pannus overgrowth according to the present invention may be obtained by providing an implantable prosthetic heart valve and an antimicrobial sewing cuff. The antimicrobial sewing cuff comprises a porous reservoir and a diffusable antimicrobial substance coupled to the reservoir that is effective for inhibiting pannus overgrowth on the heart valve after implantation. Although hydrophobic reservoirs will generally be preferred, hydrophilic reservoirs may also be used, depending upon the particular antimicrobial substance used.

The antimicrobial sewing cuff may be obtained by dissolving the diffusable antimicrobial substance in a fluid solvent to form an antimicrobial solution, which is then contacted with a porous, hydrophobic or hydrophilic reservoir. At least a portion of the diffusable antimicrobial substance is precipitated from the antimicrobial solution onto or into the reservoir, after which the fluid solvent is removed from the reservoir to obtain an antimicrobial reservoir. By incorporating the antimicrobial reservoir into a sewing cuff, an antimicrobial sewing cuff is made that can be coupled to the implantable heart valve to make a pannus overgrowth-resistant prosthetic heart valve.

In one embodiment, the antimicrobial reservoir comprises the outer covering of a sewing cuff. In another embodiment, the antimicrobial reservoir comprises an elastomeric insert or fabric member located inside the sewing cuff. A desired distribution of the antimicrobial substance(s) is achieved by selectively loading portions of the corresponding reservoir with one or more antimicrobial substances through use of a solvent such as methanol and/or a supercritical fluid solvent which comprises at least one supercritical or near-supercritical fluid.

In general, a pannus overgrowth-inhibiting antimicrobial sewing cuff useful in securing an implanted device within a patient according to the present invention comprises at least one porous reservoir, which may be either hydrophobic or hydrophilic. At least one diffusable antimicrobial substance effective for inhibiting pannus overgrowth on a device after implantation is precipitated on the reservoir, which is then incorporated into a sewing cuff having the desired property of inhibiting pannus overgrowth in vivo.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Figure 1:
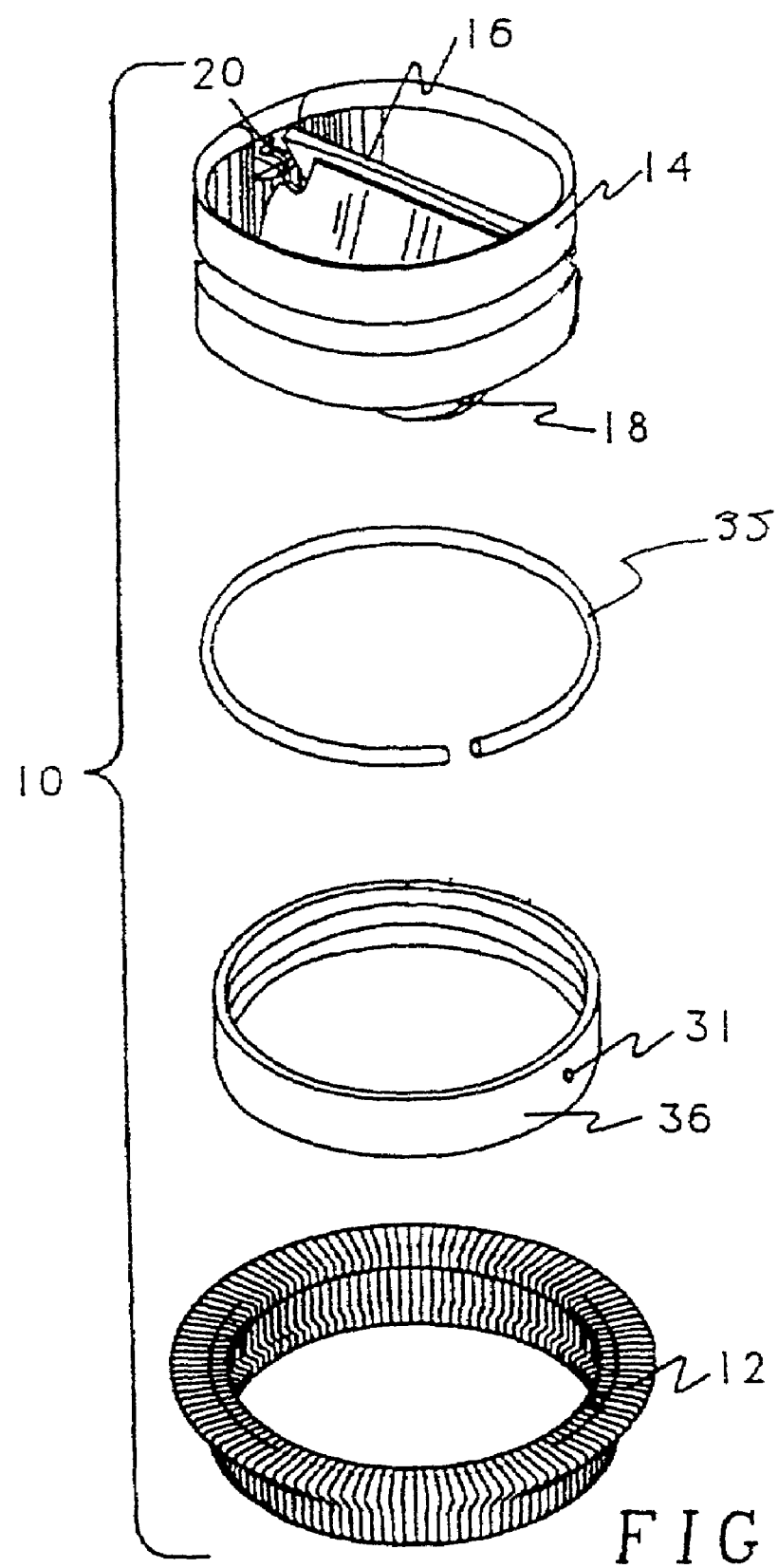
FIG. 1 is an exploded view of a prosthetic heart valve suitable for use in the present invention.

Various methods have been described for coating or otherwise incorporating antimicrobial substances onto or into medical devices for release into the local environment after the device is inserted into the body of the patient. Such prior art approaches, however, are exclusively for the purpose of suppressing infection. There is no teaching or suggestion that incorporation of antibiotic may have any effect on pannus overgrowth of an implantable medical device. Indeed, most prior art approaches are directed not toward implantable medical devices but insertable medical devices, and are intended to reduce the relatively high rates of infection associated with the use of such devices.

For example, U.S. Pat. No. 5,624,704, incorporated herein by reference, discloses methods for impregnating a non-metallic medical device with an antimicrobial substance by first dissolving the antimicrobial substance in an organic solvent to form an antimicrobial composition. Thereafter, a separate penetrating agent and alkalinizing agent is added to the antimicrobial composition. The resulting antimicrobial composition is then applied to a medical device of interest in order to incorporate the composition into the material of the medical device for post-implantation release. Significantly, the examples of the '704 patent discuss incorporation of antibiotics into urinary and venous catheters, which are not intended for long-term implantation. Incorporation of antibiotics into implantable medical devices such as heart valves and venous grafts is suggested, but no long-term data is provided. Accordingly, the issue of pannus overgrowth is not addressed by the '704 patent.

In addition to the suppression of pannus overgrowth, which has been unexpectedly discovered, antimicrobial substances incorporated into an implantable medical device may, of course, also destroy bacteria and other microorganisms. Antimicrobial substances initially applied to an implantable medical device as a solute in an organic solvent would ideally remain incorporated in a predetermined distribution within the device as the solvent is removed. Maintenance of a desired predetermined antimicrobial substance distribution within such a device is desirable to ensure predictable release kinetics for the antimicrobial substances in vivo (that is, after implantation). Predictable release kinetics are important for establishing a clinically efficacious antimicrobial local concentration around the device for an effective time period.

"Antimicrobial substance," as used herein, refers to essentially any antibiotic, antiseptic, disinfectant, etc., or combination thereof, effective for inhibiting the viability and/or proliferation of one or more microorganisms. Numerous classes of antibiotics are known and may be suitable for use in accordance with this invention. Such antibiotics may include, but are not necessarily limited to, tetracyclines (e.g., minocycline), rifamycins (e.g., rifampin), macrolides (e.g., erythromycin), penicillins (e.g., nafcillin), cephalosporins (e.g., cefazolin), other beta-lactam antibiotics (e.g., imipenem and aztreonam), aminoglycosides (e.g., gentamicin), chloramphenicol, sufonamides (e.g., sulfamethoxyazole), glycopeptides (e.g., vancomycin), quinolones (e.g., ciprofloxacin), fusidic acid, trimethoprim, metronidazole, clindamycin, mupirocin, polyenes (e.g., amphotericin B), azotes (e.g., fluconazole), and beta-lactam inhibitors.

Examples of illustrative antibiotic substances that may be used in accordance with the present invention include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, telcoplanin, mupirocin, azithromycin, clarithromycin, ofloxacin, lomefloxacin, norfloxacin, nalidixic acid, sparfloxacin, pefloxacin, amifloxacin, enoxacin, fleroxacin, ternafloxacin, tosufloxacin, clinafloxacin, sulbactam, clavulanic acid, amphotericin B, fluconazole, itraconazole, ketoconazole, nystatin, and other like compounds. The antibiotics used in accordance with this invention will generally be selected so as to have relatively low water solubility such that their period of dissolution into biological fluids is prolonged. Moreover, it may be desired for many applications that one or more antimicrobial substances having distinct modes of action be incorporated into an antimicrobial reservoir in order to achieve a broader range of antimicrobial activity.

In a preferred embodiment of the present invention, the antimicrobial substances incorporated in an antimicrobial reservoir according to this invention comprise minocycline or rifampin or a mixture thereof. Minocycline is a semisynthetic antibiotic derived from tetracycline that functions by inhibiting protein synthesis. Rifampin is a semisynthetic derivative of rifamycin B, a macrocyclic antibiotic compound produced by the mold, Streptomyces mediterranic. Rifampin inhibits bacterial DNA-dependent RNA polymerase activity and is bactericidal in nature. Both minocycline and rifampin are commercially available, are soluble in numerous organic solvents, and are active against a wide range of gram-positive and gram-negative organisms.

implantable antimicrobial medical devices such as, by way of nonlimiting example, prosthetic heart valves and annuloplasty rings having one or more sewing cuffs. Implantable antimicrobial medical devices according to the present invention comprise an implantable medical device coupled to at least one diffusable antimicrobial reservoir incorporating one or more antimicrobial substances. A desired distribution of the antimicrobial substance(s) is achieved by selectively loading portions of the corresponding reservoir with one or more antimicrobial substances through use of a solvent such as methanol and/or a supercritical fluid solvent that comprises at least one supercritical or near-supercritical fluid, preferably supercritical carbon dioxide (SCO2). In preferred embodiments, the antimicrobial substances are present in a predetermined, uniform distribution in the reservoir.

The distribution of antimicrobial substance(s) in a diffusable antimicrobial reservoir according to the present invention results in timed release of sufficient amounts of the antimicrobial substance(s) to both maintain a medically effective local concentration around the implantable antimicrobial medical device in vivo for a clinically effective period of time, and also to suppress pannus overgrowth into the valve orifice and leaflet structures. This will generally require an appropriate rate of antimicrobial diffusion from the reservoir to raise antimicrobial tissue concentrations to effective levels and/or to counteract infectious agent contamination during implantation. Thereafter, for clinically effective periods of time, one or more antimicrobial substances are released from the reservoir sufficiently rapidly to maintain a clinically effective local antimicrobial concentration without over-medication. It has advantageously been discovered that the suppression of pannus overgrowth can be effected over a range of antibiotic concentrations.

A preferred method comprises, in part, dissolving one or more antimicrobial substances in a suitable liquid solvent, such as an alcohol, ether, aldehyde, acetonitrile, or combinations thereof, to form an antimicrobial solution. The antimicrobial solution is thereafter contacted with at least a portion of an antimicrobial reservoir under conditions effective for causing incorporation of the antimicrobial substance into or onto the reservoir contacted by the antimicrobial solution. Additionally, at least one surface-active antimicrobial structure is included in the device.

In one such preferred method, the desired antimicrobial substance(s) are first dissolved in an appropriate solvent or combination of solvents to form an antimicrobial solution. Suitable solvents in this regard include essentially any aqueous or organic solvent(s) that will effectively dissolve the antimicrobial substance(s) of interest, and that are conducive to the incorporation of at least some of the dissolved antimicrobial substance(s) into an antimicrobial reservoir. The solvent is generally selected from one that will readily spread onto and/or along the particular antimicrobial reservoir surface to which it is applied. The degree of this spreading may be influenced by the surface tension of the solvent and by the surface characteristics and configuration of the material(s) of the antimicrobial reservoir(s). Illustrative examples of suitable solvents for use in this invention include, but are not necessarily limited to, C1 to C6 organic solvents such as C1 to C6 alcohols (e.g., methanol, ethanol, etc.), C1 to C6 ethers (e.g., tetrahydrofuran), C1 to C6 aldehydes, aprotic heterocyclics (e.g., n-methyl pyrrolidinone, dimethyl sulfoxide, dimethyl formamide), acetonitrile, and acetic acid.

The concentration of the antibiotic substance(s) in the antibiotic solution is not specifically restricted. Optimal concentration ranges will likely vary depending upon the particular antimicrobial substance(s) and solvent(s) used, on the conditions under which the antimicrobial solution is contacted with the antimicrobial reservoir, and on the porosity and degree of hydrophobicity/hydrophilicity of the antimicrobial reservoir, but can nonetheless be readily determined by an individual skilled in the art. In general, a higher concentration of an antimicrobial substance in the antimicrobial solution will result in greater incorporation into or onto the antimicrobial reservoir under an otherwise constant set of application conditions. However, an upper concentration limit will typically characterize a particular combination of antimicrobial solution and antimicrobial reservoir, above which further antimicrobial incorporation will become limited. Generally, the concentration of the antimicrobial substance in the antimicrobial solution is essentially in the range of about 1 mg/ml to 60 mg/ml for each antimicrobial substance present.

The antimicrobial solution of the present invention is applied to, or otherwise contacted with, at least some portion of the antimicrobial reservoir of interest in order to effect incorporation of the antimicrobial substance(s) into the reservoir. As will be apparent to the skilled individual in this art, the means by which the antimicrobial solution is contacted with the medical device is not critical, and may vary depending on the type of reservoir, its size and configuration, etc. Typically, the antimicrobial reservoirs will simply be dipped or otherwise immersed in an antimicrobial solution. Alternatively, the antimicrobial solution may be applied to the reservoir, e.g., by injection, flushing, spraying, etc. Other techniques for contacting the antimicrobial solution with the antimicrobial reservoir will be readily apparent to those skilled in the art.

Subsequent to contacting the antimicrobial solution with antimicrobial reservoir(s), the antimicrobial solution is generally allowed to remain in contact for a duration and under conditions of temperature, pressure, etc. effective to cause a desired degree of incorporation of the antimicrobial substance into or onto the reservoir(s). Of course, the optimal contact may vary depending on a number of parameters, e.g., the antimicrobial solution being used, contact temperature, etc., which can be readily determined by one skilled in the art.

Antimicrobial reservoirs are typically dried to eliminate any solvent used to incorporate antimicrobial substance(s), e.g., by air-drying, heating, vacuum drying, etc. After drying, the antimicrobial substance(s) incorporated into or onto a reservoir is not subject to substantial diffusion until implanted in vivo, or otherwise exposed to a comparable environment, wherein the incorporated antimicrobial substance becomes redissolved, and therefore more subject to diffusion from the reservoir into the surrounding (fluid) environment.

In another aspect of the invention, a method of preventing pannus overgrowth comprises use of a supercritical fluid solvent to establish a predetermined, preferably uniform distribution of one or more antimicrobial substances in a porous antimicrobial reservoir for subsequent diffusion in vivo. Prior use of a supercritical fluid solvent for making diffusable antimicrobial reservoirs, as in the present invention, has not been described or suggested by these approaches, which are not pertinent to the medical field.

SCO2 is one supercritical fluid suitable for use in the present invention. SCO2 is a powerful solvent for lipids, oils and other small molecular weight organic compounds. It is insoluble in water, and its solvating power can be controlled by changes in temperature and/or pressure as disclosed in the above references and, e.g., in U.S. Pat. No. 5,533,538, incorporated herein by reference. SCO2 is commercially used to extract flavors and oils directly from seeds and other agricultural feed materials. Issued patents also disclose its utility in forming fine particles of physiologically active substances (see, e.g., U.S. Pat. No. 5,639,441, incorporated herein by reference), and delivering such particles directly to a human or animal (see, e.g., U.S. Pat. No. 5,301,664, incorporated herein by reference). None of the foregoing references, however, disclose the use of SCO2 or other supercritical fluid in making diffusable antimicrobial reservoirs as in the present invention.

SCO2 is often used in combination with one or more adjuvants such as cosolvents (e.g., nitrous oxide or ethanol), and/or surfactants (e.g., polysorbate 80 or dipalmitoyl lecithin), as noted in the above references. Carbon dioxide itself is relatively benign environmentally, so solvent disposal costs are reduced through its use. In the present invention, the solvating power of supercritical fluid solvents preferably comprising SCO2 is controlled to cause precipitation of selected antimicrobial substances carried by such solvents in predetermined distributions within antimicrobial reservoirs. Note that where more than one antimicrobial substance of the present invention is carried by a supercritical fluid solvent, selective precipitation of each such antimicrobial substance may be obtained through control of solvent temperature and solvent ambient pressure.

Selective precipitation of antimicrobial substance(s) from a supercritical fluid solvent may be effected, for example, by either heating or cooling such solvents (depending on the solutes carried), and/or by decreasing solvent ambient pressure sufficiently to cause reversion of a solvent component to a subcritical state. In preferred embodiments, SCO2 and a supercritical cosolvent (such as nitrous oxide) may be converted from supercritical to subcritical states simultaneously or sequentially to effect selective precipitation of antimicrobial substance(s). Preheated or precooled portions of antimicrobial reservoirs may thus be made to preferentially incorporate selected antimicrobial substances.

According to another aspect of the present invention, methods are provided for producing an implantable medical device having antimicrobial properties in vivo. One such preferred method comprises, in part, dissolving one or more antimicrobial substances in a suitable supercritical fluid solvent, optionally comprising one or more cosolvents or surfactants or combinations thereof, to form a supercritical antimicrobial solution. The supercritical antimicrobial solution is thereafter incorporated into one or more porous reservoirs where one or more antimicrobial substances are precipitated in a predetermined distribution. Such precipitation is effected through application of heating, cooling or reduction in ambient pressure on the supercritical antimicrobial solution. Subsequent removal of any supercritical solvent component(s) where heating or cooling alone has been used to effect such precipitation, or of any subcritical solvent component(s) where reduction in ambient pressure has been used to effect such precipitation, yields an antimicrobial reservoir.

Disadvantages of using supercritical fluid solvents include the relatively high cost of equipment used to achieve and maintain temperatures and pressures compatible with the corresponding supercritical fluid states of solvent components. Energy costs associated with cycling between subcritical and supercritical states may also be significant. These costs can be reduced, however, if precipitation of antimicrobial substances from a supercritical antimicrobial solution is preferably achieved through heating or cooling the solution in a supercritical state, rather than through reducing ambient pressure to convert a supercritical fluid solvent component to a subcritical state.

Implantable antimicrobial medical devices of the present invention comprise one or more diffusable antimicrobial reservoirs coupled to an implantable medical device, each such reservoir comprising, for example, polyester fabric, PTFE felt, or a silicone rubber insert. Coupling of a diffusable antimicrobial reservoir to a medical device is achieved by direct coupling of the corresponding reservoir(s) to the medical device or, alternatively, by coupling to the medical device a permeable reservoir covering which itself is coupled to the corresponding reservoir(s). In preferred embodiments, the antimicrobial reservoirs are incorporated into the sewing cuff of a prosthetic heart valve (either the external covering thereof or an interior fabric/felt filler), and in the interior and/or surface of annuloplasty rings.

Coupling of such a reservoir or a permeable cover thereof to a medical device may be accomplished by, for example, bonding, sewing, clamping, fusing, clipping, and analogous techniques known to those skilled in the art. Preferred coupling techniques will depend in part on the mechanical strength required of the coupling and the inherent mechanical strength of each reservoir and/or any permeable covering thereof that may be present.

Each porous reservoir incorporates (as, for example, by adsorption and/or mechanical trapping of crystallized antimicrobial substances) one or more diffusable antimicrobial substances. Each such substance is subject to controlled release in vivo as a solute in biological fluid which penetrates the reservoir and which also communicates with biological fluid adjacent to the implanted device.

Time periods during which a diffusable antimicrobial substance is released from an antimicrobial reservoir of the present invention are predetermined, in part, by choice of the porosity of the reservoir material (e.g., polyester fabric and/or PTFE felt or silicone rubber elastomer inserts), as well as the molecular weight, polarity, distribution and concentration of diffusable substance(s) incorporated within the reservoir. Preferred choices for diffusable antimicrobial substances include, but are not limited to, silver sulfadiazine, silver nitrate, rifampin, minocycline, or chlorhexidene diacetate. Other factors that may determine the release kinetics of such antimicrobial substances to obtain an effective local concentration around the device in vivo include the nature of the tissue and/or biological fluids through which diffusion takes place, as well as the flow rates of the relevant biological fluids.

An implantable device such as a heart valve, which is intended to contact both biological fluids and substantially solid tissue, may preferably comprise two or more different diffusable antimicrobial reservoirs. Incorporating different diffusable antimicrobial substances having (optionally) different diffusion rates in multiple diffusable antimicrobial reservoirs may serve, in selected applications, to more effectively inhibit microbial activity in the respective tissue (s) and fluid(s) contacting an implanted antimicrobial medical device and/or to improve the resistance to pannus overgrowth of the implantable medical device. Thus, for example, microbial inhibition can be more accurately tailored to type, location, and order of appearance of clinically important infectious agent potentially affecting an implanted device within the period of early-onset infection (generally within 60 days of implantation).

FIG. 1 schematically illustrates an implantable heart valve 10 suitable for use in the present invention. The valve 10 comprises an orifice member 14, a stiffening ring 36 and a sewing cuff 12. Stiffening ring 36 is coupled to orifice member 14 by a lock wire 35. Orifice member 14 further comprises a pair of opposed leaflets 18, pivotally coupled to the orifice member at pivot location 20. Opposed leaflets 18 open and close the valve in response to the pumping action of the heart.

Figure 2:
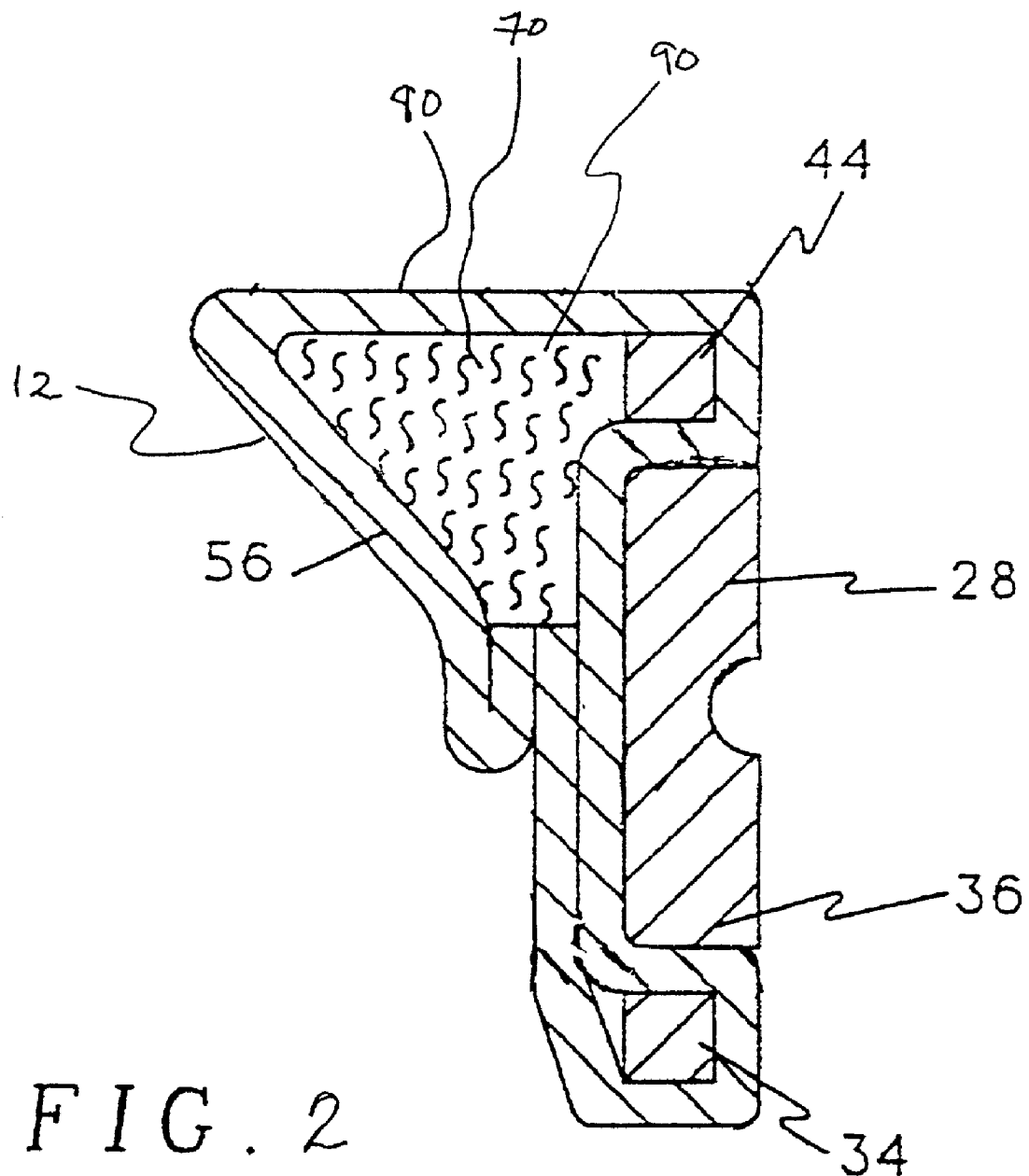
FIG. 2 illustrates a portion of an antimicrobial prosthetic heart valve suitable for use in the present invention, depicting the sewing cuff and stiffening ring in cross-section.

Sewing cuff 12 may be coupled to stiffening ring 36 by retainer rings 34, 44 (FIG. 2). Sewing cuff 12 comprises an outer fabric covering 56 of permeable polyester fabric. In one embodiment of the present invention, outer fabric covering 56 of sewing cuff 12 functions as an antimicrobial reservoir 80 for incorporating an antimicrobial substance.

FIG. 2 illustrates a portion of a prosthetic heart valve suitable for use in the present invention, including the sewing cuff and stiffening ring, in cross-section. Sewing cuff 12 comprises an inner Teflon felt filler member 70. In another embodiment of the invention, filler member 70 functions as an antimicrobial reservoir 90 for an antimicrobial substance in an amount effective to prevent pannus overgrowth into orifice member 14 and leaflets 18.

Incorporation of the antimicrobial substance into or onto the antimicrobial reservoir 80, 90 is in a predetermined advantageous distribution. The antimicrobial substance thus incorporated into an implantable antimicrobial medical device according to the present invention exhibits clinically desirable antimicrobial release kinetics from the medical device after exposure to an in vivo environment. Consequently, such medical devices are less susceptible to microbial colonization following implantation.

Phrases such as "incorporated into" and "incorporating into" as used herein mean that at least some diffusable antimicrobial substance permeates, adheres to, resides within, or otherwise becomes associated with one or more of the porous, hydrophobic or hydrophilic reservoirs of which the implantable medical device is preferably comprised. Thus, such a diffusable antimicrobial substance may be largely associated with the surface of a reservoir (as in a coating), may penetrate within or between the pores of the reservoir, may be covalently or ionically bound to the reservoir structure, or may be otherwise coupled to the reservoir in a manner to provide a predictable diffusion stream of the antimicrobial substance following implantation of the device. The preferred nature of the association between diffusable antimicrobial substance(s) and antimicrobial reservoir(s) of the present invention depends on the particular diffusable antimicrobial substance used, the antimicrobial activity (including, for example, release kinetics) desired in the implanted antimicrobial medical device, and/or the type and structure of the medical device itself.

The diffusable fraction of antimicrobial substance(s) incorporated into or onto the antimicrobial reservoir of an implantable antimicrobial medical device may be evaluated by, for example, mass analysis of the reservoir or of the entire device before and after treatment. Alternatively, the incorporated antimicrobial substance remaining after treatment may be extracted or otherwise removed from the device using an appropriate method, to be compared with the amount initially incorporated.

An implantable antimicrobial medical device made and/or used in accordance with the present invention may be selected from any of the numerous device types available to the medical practitioner, including cardiovascular devices, orthopedic implants, and a variety of other prosthetic devices. Examples of such devices may include, but are not limited to, annuloplasty rings, heart valve sewing cuffs, pericardial patches, vascular grafts, and other like devices. Additional examples may include fixator pins, femoral prostheses, acetabular prostheses, dental prostheses and the like.

Implantable antimicrobial medical devices of the present invention may include essentially any implantable medical device coupled to one or more antimicrobial reservoirs wherein effective incorporation of an antibiotic substance can be achieved. These may include medical devices comprised of thermoplastic or polymeric materials such as rubber, plastic, polyethylene, polyurethane, silicone, polytetrafluoroethylene, polyethylene terepthalate, latex, elastomers, and other like materials. These may also include metals (e.g., titanium, cobalt-chromium, stainless steel) and ceramics (hydroxyapetite, pyrolytic carbon) in cancellous, i.e., porous, configurations.

Many such medical devices contain at least some materials in a fabric or fabric-like form which may overlay, contain, and give shape to an antimicrobial reservoir, as well as coupling the reservoir to the corresponding medical device. Such fabric and fabric-like materials preferably comprise polymeric fibers comprised of polytetrafluoroethylene, polyethylene terephthalate, and other like materials. Examples of such devices which contain at least some of these materials may include, but are not limited to, annuloplasty rings, heart valve sewing cuffs, pericardial patches, vascular grafts, etc.

In using preferred embodiments of the present invention for treating a patient, an implantable antimicrobial medical device is implanted which exhibits diffusion of one or more antimicrobial substances from the device for some period of time after the device has been exposed to an in vivo environment. The release kinetics of the antimicrobial substance(s) from the device may be evaluated using any one of a variety of approaches.

The antimicrobial release kinetics and/or activity from an antimicrobial reservoir are generally sustained for an extended number of days, or even weeks. In this way, a patient's susceptibility to post-operative infection may be reduced for a clinically relevant duration following device implantation, in addition to controlling pannus tissue overgrowth.

EXAMPLE 1

Pannus Overgrowth Onto a Mechanical Heart Valve in an Animal Study

The mitral valve of a 176 day old, 63 kg male sheep was replaced with a size 29 mitral model St. Jude Medical mechanical heart valve (CAP-1). The techniques used for the implant study followed E. D. Irwin et al., "Long Term Evaluation of Prosthetic Mitral Valves In Sheep," J. Invest. Surgery, 6, 133–141 (1993). The surgical procedure was uneventful and the animal recovered in the normal fashion.

Figure 3:
FIG. 3 is a color photograph of an explanted, untreated control heart valve (CAP-1) after 181 days in a juvenile sheep implant study.

After surgery, the animal was transferred to the farm. Throughout the long-term holding period, the animal was healthy. On postoperative day 181, the animal was sacrificed and the valve removed for pathological examination. Upon gross examination, pannus was observed protruding over the orifice of the valve (FIG. 3). Accordingly, untreated mechanical valves have been demonstrated to be susceptible to pannus overgrowth.

EXAMPLE 2

Preparation of Antibiotic Treated Heart Valve for Phase I Animal Study

To prevent accumulation of antibiotic between rotatable components of the heart valve, the inner diameters of mitral valve sewing cuff sub-assemblies of Carbomedics CPH-VTM 27 mm heart valves were masked by placing silicone elastomer plugs in the cuff sub-assembly. To improve masking characteristics, the silicone elastomer masks were placed under a compressive load to expand the plug to obtain an intimate contact with the inner diameter of the sewing cuff sub-assembly.

Antibiotic solution was prepared by mixing/dissolving 7.5 and 12.0 grains of minocycline and rifampin, respectively, into 300 ml of methanol at 45° C. Solution concentrations were measured by High Performance Liquid Chromatography (HPLC) to be 25.1 mg/ml and 45.6 mg/ml for minocycline and rifampin, respectively. Using syringes, sewing cuff assemblies were then injected at six locations with a total of 2.15 ml of the antibiotic solution and allowed to dry overnight before assembling into a final heart valve assembly.

Seven valves were prepared according to the foregoing protocol. These seven valves, along with one untreated control valve, were implanted for 90–98 days (nominal 90 day implantation time) in the mitral position of juvenile sheep. The techniques used for the implant study followed E. D. Irwin et al., "Long Term Evaluation of Prosthetic Mitral Valves In Sheep," J. Invest. Surgery, 6, 133–141 (1993). Briefly, juvenile sheep (30–35 kg to ensure good valve size fit) were selected. The native mitral valve was excised from the animal during surgery and replaced with a CPHVTM 27 mm heart valve of the present invention, or an untreated CPHV control valve of the same size.

Figure 4:
FIG. 4 is a color photograph of an explanted untreated control heart valve (CPHV-1) after 90 days in a juvenile sheep implant study different from the study involving the valve of FIG. 3.
Figure 5:
FIG. 5 is a color photograph of an explanted heart valve (CPHV-7) treated according to the present invention after 90 days in the same juvenile sheep implant study as the valve of FIG. 4.

After the nominal 90 day implantation period, the animals were sacrificed and the explanted valves photographed and prepared for pathological evaluation. Upon gross examination, pannus was observed protruding over the orifices of the control valve (CPHV-1, FIG. 4). For the treated valves prepared according to the present invention, on the other hand, pannus growth stopped at the orifice rim on the valves, as shown in FIG. 5 (CPHV-7).

EXAMPLE 3

Preparation of Antibiotic Treated Heart Valve for Phase II Animal Study

The inner diameters of mitral valve sewing cuff sub-assemblies were masked with silicone elastomer plugs according to the procedure described in Example 2.

Antibiotic solution was prepared by mixing/dissolving 12.6 and 20.1 grams of minocycline and rifampin, respectively, into 300 ml of methanol at 45° C. Solution concentrations were measure to be 44.4 mg/ml and 75.2 mg/ml for minocycline and rifampin, respectively. Using syringes, sewing cuff assemblies were then injected at six locations with a total of 1.69 ml of solution and allowed to dry overnight before assembling into a final heart valve assembly.

Six CPHVTM 27 mm heart valves were prepared according to the foregoing protocol, and implanted, along with two untreated control valves, for 90–98 days (nominal 90 day implantation time) in the mitral position of juvenile sheep according to the protocol of Example 2.

Figure 6:
FIG. 6 is a color photograph of an explanted untreated control heart valve (CPHV-19) after 91 days in a juvenile sheep implant study different from the studies involving the valves of FIGS. 3, 4 and 5.
Figure 7:
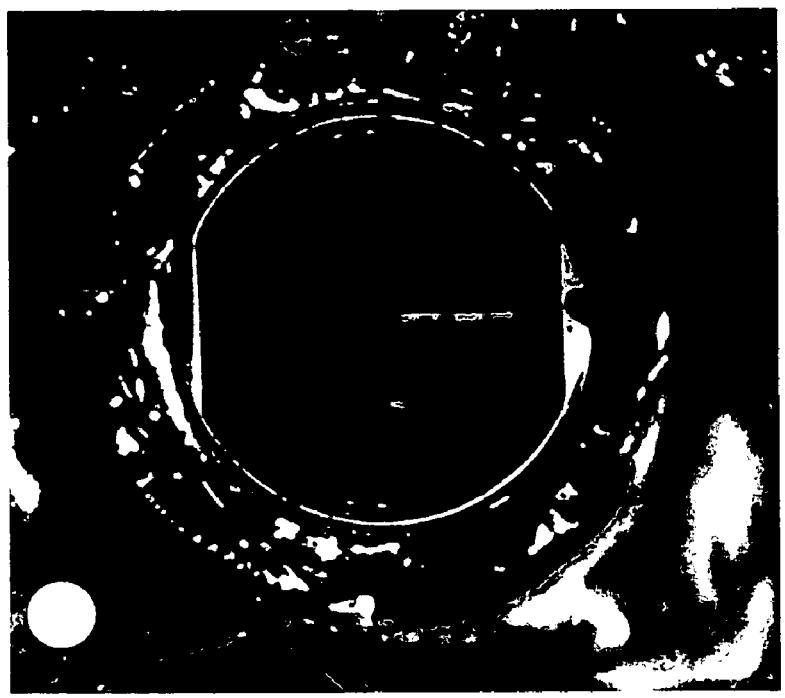
FIG. 7 is color photograph of an explanted heart valve (CPHV-14) treated according to the present invention after 90 days in the same juvenile sheep implant study as the valve of FIG. 6.

After the 90 day nominal implantation period, the animals were sacrificed and the explanted valves photographed and prepared for pathological evaluation. Upon gross examination, pannus was observed protruding over the orifices of the control valves (see FIG. 6, CPHV-19). Pannus growth in the treated valves stopped at the orifice rim of the valves, as shown in FIG. 7 (CPHV-14).

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

We claim:

1. A method of providing resistance to pannus overgrowth to an implantable prosthetic heart valve comprising:
   A) providing an implantable heart valve comprising a valve orifice defining a blood flow area, a leaflet coupled to said orifice for movement between an open position and a closed position, and a sewing cuff coupled to said orifice, said sewing cuff comprising a material suitable for retaining an antibiotic;
   B) providing an antibiotic solution comprising minocycline and rifampin dissolved in a solvent, wherein said solvent comprises SCO2;
   C) contacting said material suitable for retaining an antibiotic and said antibiotic solution to obtain an antimicrobial reservoir;
   D) removing the solvent from said antimicrobial reservoir; and
   E) implanting said heart valve.

2. The method of claim 1 wherein said solvent comprises a cosolvent selected from the group consisting of C1 to C6 alcohols, C1 to C6 ethers, C1 to C6 aldehydes, pyrrolidinones, dimethyl sulfoxide, dimethyl formamide, acetonitrile, and acetic acid.

3. A method of providing resistance to pannus overgrowth to an implantable prosthetic heart valve comprising:
   a) providing a sewing cuff comprising a material suitable for retaining an antibiotic;
   b) providing an antibiotic solution comprising minocycline and rifampin dissolved in a solvent, wherein said solvent comprises SCO2;
   c) contacting said material suitable for retaining an antibiotic and said antibiotic solution to obtain a sewing cuff comprising an antimicrobial reservoir;
   d) removing the solvent from said antimicrobial reservoir;
   e) providing an implantable heart valve comprising a valve orifice having an interior surface defining a flow area, an exterior peripheral surface, and a leaflet coupled to said orifice for movement between an open position and a closed position;
   f) coupling said sewing cuff to said exterior peripheral surface of said heart valve; and
   g) implanting said heart valve.

4. The method of claim 3 wherein said solvent comprises a cosolvent selected from the group consisting of C1 to C6 alcohols, C1 to C6 ethers, C1 to C6 aldehydes, pyrrolidinones, dimethyl sulfoxide, dimethyl formamide, acetonitrile, and acetic acid.

* * * * *